(12) United States Patent
Nakagawa

(10) Patent No.: US 6,900,326 B2
(45) Date of Patent: May 31, 2005

(54) METHOD OF PRODUCING N-ALKOXYCARBONYLPIPERIDINE DERIVATIVE, NEW COMPOUND AS RAW MATERIAL THEREFOR, AND METHOD OF PRODUCING THE COMPOUND

(75) Inventor: Kiyono Nakagawa, Tokyo (JP)

(73) Assignee: Yuki Gosei Kogyo Co., Ltd., Tokyo (JP)

( * ) Notice: Subject to any disclaimer, the term of this patent is extended or adjusted under 35 U.S.C. 154(b) by 56 days.

(21) Appl. No.: 10/664,074

(22) Filed: Sep. 17, 2003

(65) Prior Publication Data

US 2004/0063953 A1 Apr. 1, 2004

(30) Foreign Application Priority Data

Sep. 18, 2002 (JP) ......................................... 2002-272173

(51) Int. Cl.[7] ..................... C07D 211/22; C07D 211/32; C07D 211/44
(52) U.S. Cl. ....................... 546/188; 546/189; 546/190; 546/191
(58) Field of Search ................................. 546/188, 189, 546/190, 191

(56) References Cited

U.S. PATENT DOCUMENTS 6,288,233 B1    9/2001   Kuo et al. ..................... 546/93
6,307,048 B1   10/2001   Kuo et al. ..................... 546/93

Primary Examiner—Ba K. Trinh
(74) Attorney, Agent, or Firm—Birch, Stewart, Kolasch & Birch, LLP

(57) ABSTRACT

A method of producing an N-alkoxycarbonylpiperidine derivative, comprising reacting an N-aralkylpiperidine derivative represented by the following general formula (1):

wherein $R^1$ represents an aralkyl group which may have a substituent, with a mesyl halide in the presence of a base, thereby obtaining a mesylated product represented by the following general formula (2):

wherein $R^1$ represents an aralkyl group which may have a substituent and Ms represents a mesyl group, and
reacting the mesylated product with a dicarbonate represented by the following general formula (3):

wherein $R^4$ represents an alkyl group, in the presence of hydrogen and a catalyst containing palladium, thereby obtaining an N-alkoxycarbonylpiperidine derivative represented by the following general formula (4):

wherein $R^4$ represents an alkyl group and Ms represents a mesyl group.

22 Claims, No Drawings

METHOD OF PRODUCING N-ALKOXYCARBONYLPIPERIDINE DERIVATIVE, NEW COMPOUND AS RAW MATERIAL THEREFOR, AND METHOD OF PRODUCING THE COMPOUND

CROSS-REFERENCE TO RELATED APPLICATIONS

This application is based upon and claims the benefit of priority from the prior Japanese Patent Application No. 2002-272173, filed Sep. 18, 2002, the entire contents of which are incorporated herein by reference.

BACKGROUND OF THE INVENTION

1. Field of the Invention

The present invention relates to a method of producing an N-alkoxycarbonylpiperidine derivative, which is useful as an intermediate of a drug.

2. Description of the Related Art

In U.S. Pat. No. 6,288,233 (column 23) and U.S. Pat. No. 6,307,048 (column 25), it is disclosed that an N-alkoxycarbonylpiperidine derivative, which is represented by the following general formula (4):

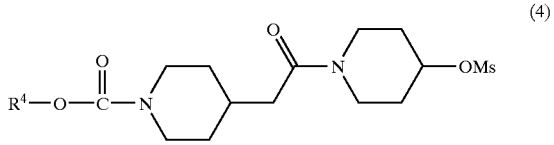

(wherein $R^4$ represents an alkyl group and Ms represents a mesyl group) and whose typical example is 1-(1-tert-butoxycarbonyl-4-piperidylacetyl)-4-mesyloxypiperidine, is useful as an intermediate in a synthesis process of a drug, e.g., an anticancer drug SCH-66336. However, there has been no report on a method of producing the N-alkoxycarbonylpiperidine derivative.

Examples of a method of producing the N-alkoxycarbonylpiperidine derivative include a method comprising: reacting N-alkoxycarbonyl-4-piperidineacetic acid with 4-hydroxypiperidine, thereby obtaining 1-(1-alkoxycarbonyl-4-piperidylacetyl)-4-hydroxypiperidine; and mesylating the product by using mesyl halide.

In general, in a condensation reaction between a carboxylic acid and an amine, a method of using a condensing agent such as dicyclohexylcarbodiimide (DCC) and a mixed acid anhydride method of using isobutyloxycarbonyl chloride or the like, are employed. However, if a condensing agent is used in the aforementioned reaction of N-alkoxycarbonyl-4-piperidineacetic acid with 4-hydroxypiperidine, there will arise problems such as that the condensing agent is costly and that the yield of the target product is significantly decreased due to generation of acylurea-type side products and such side products have to be removed. On the other hand, if the mixed acid anhydride method is employed in the reaction of N-alkoxycarbonyl-4-piperidineacetic acid with 4-hydroxypiperidine, the reaction must be carried out at a low temperature (−15° C. or so) in a solvent which has been thoroughly dehydrated in order to suppress any side reaction.

BRIEF SUMMARY OF THE INVENTION

An object of the present invention is to provide a method of producing an N-alkoxycarbonylpiperidine derivative, a new compound as a raw material for the derivative, and a method of producing the compound.

In order to solve the problems described above, the inventors of the present invention keenly studied a method of producing an N-alkoxycarbonylpiperidine derivative at a sufficiently high yield in industrial terms, and discovered a new N-aralkylpiperidine derivative which is useful as a raw material for the target derivative, thereby completing the present invention.

In a first aspect of the present invention, there is provided a method of producing an N-alkoxycarbonylpiperidine derivative, comprising:

reacting an N-aralkylpiperidine derivative represented by the following general formula (1):

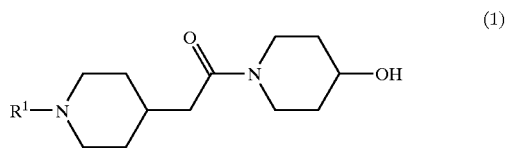

wherein $R^1$ represents an aralkyl group which may have a substituent, with a mesyl halide in the presence of a base, thereby obtaining a mesylated product represented by the following general formula (2):

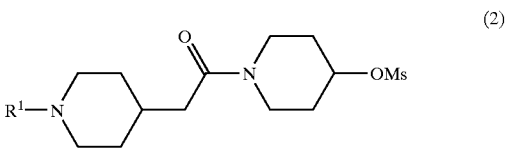

wherein $R^1$ represents an aralkyl group which may have a substituent and Ms represents a mesyl group; and reacting the mesylated product with a dicarbonate represented by the following general formula (3):

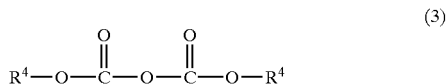

wherein $R^4$ represents an alkyl group, in the presence of hydrogen and a catalyst containing palladium, thereby obtaining an N-alkoxycarbonylpiperidine derivative represented by the following general formula (4):

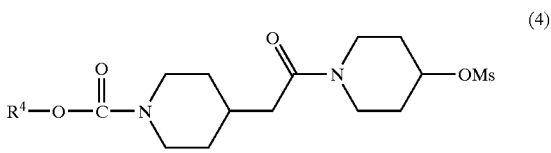

wherein $R^4$ represents an alkyl group and Ms represents a mesyl group.

In a second aspect of the present invention, there is provided a method of producing an N-alkoxycarbonylpiperidine derivative, comprising:

reacting an N-aralkylpiperidine derivative represented by the following general formula (1):

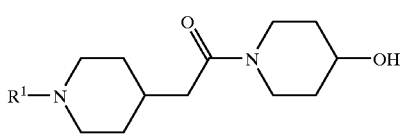

(1)

wherein $R^1$ represents an aralkyl group which may have a substituent, with a dicarbonate represented by the following general formula (3):

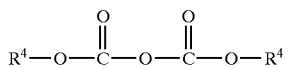

(3)

wherein $R^4$ represents an alkyl group, in the presence of hydrogen and a catalyst containing palladium, thereby obtaining an alkoxycarbonylated product represented by the following general formula (5):

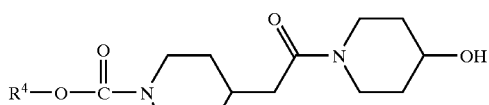

(5)

wherein $R^4$ represents an alkyl group; and reacting the alkoxycarbonylated product with a mesyl halide in the presence of a base, thereby obtaining an N-alkoxycarbonylpiperidine derivative represented by the following general formula (4):

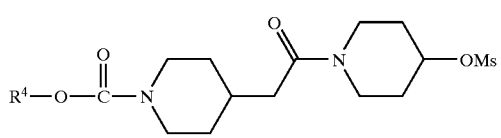

(4)

wherein $R^4$ represents an alkyl group and Ms represents a mesyl group.

In a third aspect of the present invention, there is provided an N-aralkylpiperidine derivative represented by the following general formula (1):

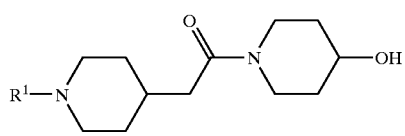

(1)

wherein $R^1$ represents an aralkyl group which may have a substituent.

In a fourth aspect of the present invention, there is provided a method of producing an N-aralkylpiperidine derivative, comprising:

reacting an N-aralkylpiperidone derivative represented by the following general formula (6):

(6)

wherein $R^1$ represents an aralkyl group which may have a substituent, with a phosphate reagent represented by the following general formula (7):

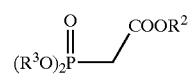

(7)

wherein $R^2$ represents an alkyl group and $R^3$ represents an alkyl group or aryl group, in the presence of a base, thereby obtaining a piperidylideneacetic acid derivative represented by the following general formula (8):

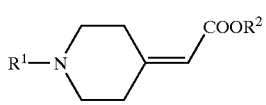

(8)

wherein $R^1$ represents an aralkyl group which may have a substituent and $R^2$ represents an alkyl group;

reducing the piperidylideneacetic acid derivative to a piperidylacetic acid derivative represented by the following general formula (9):

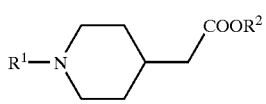

(9)

wherein $R^1$ represents an aralkyl group which may have a substituent and $R^2$ represents an alkyl group; and reacting the piperidylacetic acid derivative with 4-hydroxypiperidine in the presence of a base, thereby obtaining an N-aralkylpiperidine derivative represented by the following general formula (1):

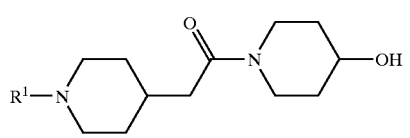

(1)

wherein $R^1$ represents an aralkyl group which may have a substituent.

In a fifth aspect of the present invention, there is provided a method of producing 1-(4-piperidylacetyl)-4-hydroxypiperidine represented by the following formula (10):

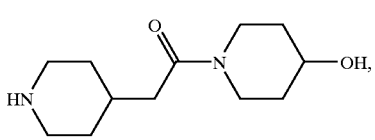

(10)

comprising:
de-aralkylating an N-aralkylpiperidine derivative of the following general formula (1):

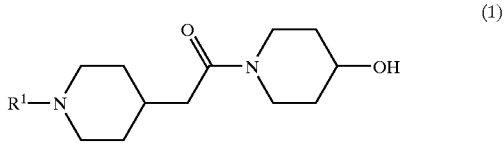

(1)

wherein $R^1$ represents an aralkyl group which may have a substituent.

In a sixth aspect of the present invention, there is provided 1-(4-piperidylacetyl)-4-hydroxypiperidine represented by the following formula (10):

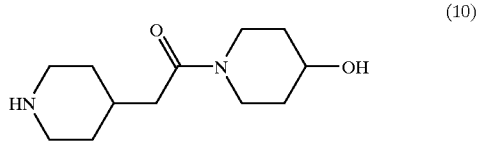

(10)

According to the present invention, an N-alkoxycarbonylpiperidine derivative represented by the general formula (4), which is useful as an intermediate of a drug, can be produced at sufficiently high yield in industrial terms. Further, in the process of producing the N-alkoxycarbonylpiperidine derivative, two types of novel compounds, an N-aralkylpiperidine derivative represented by the general formula (1) and 1-(4-piperidylacetyl)-4-hydroxypiperidine represented by the formula (10), can be provided, and each method of producing each of these novel compounds can be also provided in the present invention.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

DETAILED DESCRIPTION OF THE INVENTION

In the present specification, the "aralkyl group which may have a substituent" is preferably a benzyl group which may have a substituent. Examples of the "aralkyl group which may have a substituent" include a benzyl group, an α-methylbenzyl group, a p-methylbenzyl group, a p-nitrobenzyl group and a p-methoxybenzyl group. Examples of the substituent on the aralkyl group include a halogen atom, an alkyl group, an alkoxy group, an acyl group, an alkoxycarbonyl group and a nitro group.

In the present specification, the "alkyl group (i.e., the alkyl group represented by each of $R^2$, $R^3$ and $R^4$)" is preferably a straight-chain or branched alkyl group having 1 to 6 carbon atoms, and examples thereof include a methyl group, an ethyl group, a propyl group, an isopropyl group, an n-butyl group, an isobutyl group, a tert-butyl group, an n-pentyl group, a tert-pentyl group and a hexyl group. Examples of the "aryl group" represented by $R^3$ include a phenyl group.

$R^2$ is more preferably a methyl group or an ethyl group and most preferably an ethyl group. $R^3$ is more preferably a methyl group, an ethyl group or a phenyl group and most preferably an ethyl group. $R^4$ is most preferably a tert-butyl group.

According to a method of the present invention described below, the N-aralkylpiperidine derivative represented by the aforementioned general formula (1) can be produced.

In a first step (Step 1) of the method, a piperidone derivative represented by the aforementioned general formula (6) is reacted with a phosphate reagent represented by the aforementioned general formula (7) in the presence of a base, whereby a piperidylideneacetic acid derivative represented by the aforementioned general formula (8) is obtained.

Examples of the phosphate reagent include methyl dimethylphosphonoacetate, ethyl diethylphosphonoacetate, ethyl diphenylphosphonoacetate and the like. Ethyl diethylphosphonoacetate is preferable. With regard to the amount of the phosphate reagent to be used, the stoichiometric amount with respect to the piperidone derivative, i.e., the equimolar amount to the piperidone derivative will generally be enough. The amount of the phosphate reagent to be used is preferably 1 to 1.5 times as much as the stoichiometric amount with respect to the piperidone derivative.

Examples of the base include sodium methoxide, potassium methoxide, sodium ethoxide, potassium ethoxide, sodium tert-butoxide, potassium tert-butoxide, sodium hydride, potassium hydride, sodium carbonate, potassium carbonate, sodium hydroxide and potassium hydroxide. Among these examples, alkali metal alkoxides such as sodium methoxide and sodium ethoxide are preferable. With regard to the amount of the base to be used, the stoichiometric amount with respect to the piperidone derivative, i.e., the equimolar amount to the piperidone derivative will generally be enough. The amount of the base to be used is preferably 1 to 1.2 times as much as the stoichiometric amount with respect to the piperidone derivative.

The reaction of the first step (Step 1) can be generally carried out by using a solvent. When a solvent is used, the type of the solvent is not particularly restricted unless the solvent disturbs the reaction. Examples of the solvent include: alcohols such as methanol, ethanol, 2-propanol, n-butanol and tert-butanol; ethers such as diethyl ether, tetrahydrofuran and dioxane; hydrocarbons such as benzene, toluene and xylene; and nitrites such as acetonitrile. The aforementioned examples of the solvent may be used either singly or in the form of a combination of two or more types of them.

The reaction temperature may vary depending on the raw materials for the reaction (i.e., the materials involved in the reaction including the solvent). The reaction temperature is generally in the range of −10 to 30° C. The reaction time varies according to the raw materials, the reaction temperature or the like. The reaction is normally completed within 1 to 5 hours.

Next, in a second step (Step 2) of the method, the piperidylideneacetic acid derivative represented by the aforementioned general formula (8) is subjected to a reducing reaction, whereby a piperidylacetic acid derivative represented by the aforementioned general formula (9) is obtained.

The aforementioned reducing reaction can be effected by using a catalyst. The type of the catalyst is not particularly restricted as long as it is a catalyst containing a metal which belongs to Group VIII of the periodic table. Examples of the catalyst include: a catalyst containing platinum such as platinum oxide, platinum black, platinum-carbon and platinum-alumina; a catalyst containing palladium such as palladium black, palladium-carbon, palladium-alumina and palladium-barium sulfate; a catalyst containing rhodium such as rhodium oxide, rhodium-carbon and rhodium-alumina; a catalyst containing ruthenium such as ruthenium oxide, ruthenium-carbon and ruthenium-alumina; and a catalyst containing nickel such as Raney nickel and reduced nickel. Among these examples, a catalyst containing platinum, a catalyst containing palladium and a catalyst containing rhodium are preferable. Use of a catalyst containing platinum is the most preferable. In this case, a specific example of the most preferable catalyst is platinum-carbon. With regard to the amount of the catalyst to be used (as the amount converted to an amount of metal), only a small amount of the catalyst, with respect to the piperidylideneacetic acid derivative, will be enough. The amount of the catalyst to be used is preferably in the range of 0.01 to 0.5 mass % of the piperidylideneacetic acid derivative. The hydrogen pressure is not particularly restricted. The hydrogen pressure is preferably in the range of normal pressure to 1 MPa.

The reaction of the second step (Step 2) can be generally carried out by using a solvent. When a solvent is used, the type of the solvent is not particularly restricted unless the solvent disturbs the reaction. Examples of the solvent include: alcohols such as methanol, ethanol, 2-propanol, n-butanol and tert-butanol; esters such as ethyl acetate and ethyl propionate; ethers such as diethyl ether, tetrahydrofuran and dioxane; and hydrocarbons such as benzene, toluene and xylene. The aforementioned examples of the solvent may be used either singly or in the form of a combination of two or more types of them.

The reaction temperature may vary depending on the raw materials for the reaction (i.e., the materials involved in the reaction including the solvent). The reaction temperature is generally in the range of 30 to 90° C. The reaction time varies according to the raw materials, the reaction temperature or the like. The reaction is normally completed within 1 to 10 hours.

Subsequently, in a third step (Step 3) of the method, the piperidylacetic acid derivative represented by the aforementioned general formula (9) is reacted with 4-hydroxypiperidine in the presence of a base, whereby an N-aralkylpiperidine derivative represented by the aforementioned general formula (1) is obtained.

With regard to the amount of 4-hydroxypiperidine to be used, the stoichiometric amount with respect to the piperidylacetic acid derivative, i.e., the equimolar amount to the piperidylacetic acid derivative will generally be enough. The amount of 4-hydroxypiperidine to be used is preferably 1 to 1.5 times as much as the stoichiometric amount with respect to the piperidylacetic acid derivative.

Examples of the base include sodium methoxide, potassium methoxide, sodium ethoxide, potassium ethoxide, sodium tert-butoxide, potassium tert-butoxide, sodium hydride, potassium hydride, sodium carbonate, potassium carbonate, sodium hydroxide and potassium hydroxide. Among these examples, alkali metal alkoxides such as sodium methoxide and sodium ethoxide are preferable. With regard to the amount of the base to be used, the amount which is approximately equimolar to the piperidylacetic acid derivative will generally be enough. The amount of the base to be used is preferably 0.5 to 1.5 times as much as the equimolar amount with respect to the piperidylacetic acid derivative.

The reaction of the third step (Step 3) can be generally carried out by using a solvent. When a solvent is used, the type of the solvent is not particularly restricted unless the solvent disturbs the reaction. Examples of the solvent include: alcohols such as methanol, ethanol, 2-propanol, n-butanol and tert-butanol; ethers such as diethyl ether, tetrahydrofuran and dioxane; and hydrocarbons such as benzene, toluene and xylene. The aforementioned examples of the solvent may be used either singly or in the form of a combination of two or more types of them.

The reaction temperature may vary depending on the raw materials for the reaction (i.e., the materials involved in the reaction including the solvent). The reaction temperature is generally in the range of 50 to 120° C. The reaction time varies according to the raw materials, the reaction temperature or the like. The reaction is normally completed within 1 to 10 hours.

The N-aralkylpiperidine derivative represented by the aforementioned general formula (1) is then subjected to mesylation and alkoxycarbonylation, so that the N-alkoxycarbonylpiperidine derivative represented by the aforementioned general formula (4) is obtained. The order of the mesylation step and the alkoxycarbonylation step does not matter. That is, either the following first method (comprising the mesylation step and the alkoxycarbonylation step in this order) or the second method (comprising the alkoxycarbonylation step and the mesylation step in this order) may be employed.

[First Method]

The first method comprises: a mesylation step (Step 4a) of reacting a the N-aralkylpiperidine derivative represented by the aforementioned general formula (1) with a mesyl halide in the presence of a base, thereby obtaining a mesylated product represented by the aforementioned general formula (2); and then a alkoxycarbonylation step (Step 5a) of reacting the mesylated product with a dicarbonate represented by the aforementioned general formula (3) in the presence of hydrogen and a catalyst containing palladium, thereby obtaining an N-alkoxycarbonylpiperidine derivative represented by the aforementioned general formula (4).

First, in the mesylation step (Step 4a) of the first method, an N-aralkylpiperidine derivative represented by the aforementioned general formula (1) is reacted with a mesyl halide in the presence of a base, whereby a mesylated product represented by the aforementioned general formula (2) is obtained.

Examples of the mesyl halide include mesyl chloride. Examples of the base include pyridine, dimethylamine, diethylamine, triethylamine, tributylamine and triethanolamine.

With regard to the amount of the base to be used, the stoichiometric amount with respect to the mesyl halide, i.e., the equimolar amount to the mesyl halide will generally be enough. The amount of the base to be used is preferably 1 to 1.5 times as much as the stoichiometric amount with respect to the mesyl halide.

With regard to the amount of mesyl halide to be used, the stoichiometric amount with respect to the N-aralkylpiperidine derivative, i.e., the equimolar amount to the N-aralkylpiperidine derivative will generally be enough. The amount of mesyl halide to be used is preferably 1 to 1.5 times as much as the stoichiometric amount with respect to the N-aralkylpiperidine derivative.

The reaction of the mesylation step (Step 4a) can be generally carried out by using a solvent. When a solvent is used, the type of the solvent is not particularly restricted unless the solvent disturbs the reaction. Examples of the solvent include: esters such as ethyl acetate and ethyl propionate; ethers such as diethyl ether, tetrahydrofuran and dioxane; hydrocarbons such as benzene, toluene and xylene; halogenated hydrocarbons such as dichloromethane, dichloroethane and chloroform; and nitriles such as acetonitrile. The aforementioned examples of the solvent may be used either singly or in the form of a combination of two or more types of them.

The reaction temperature may vary depending on the raw materials for the reaction (i.e., the materials involved in the reaction including the solvent). The reaction temperature is generally in the range of −10 to 20° C. The reaction time varies according to the raw materials, the reaction temperature or the like. The reaction is normally completed within 1 to 5 hours.

Next, in the alkoxycarbonylation step (Step 5a) of the first method, the mesylated product obtained in the former Step 4a is reacted with a dicarbonate represented by the aforementioned general formula (3) in the presence of hydrogen and a catalyst containing palladium, whereby an N-alkoxycarbonylpiperidine derivative represented by the aforementioned general formula (4) can be obtained. In this Step 5a, de-aralkylation and alkoxycarbonylation can be carried out in "one pot".

Examples of the dicarbonate include dimethyl dicarbonate, diethyl dicarbonate, dipropyl dicarbonate, diisopropyl dicarbonate, dibutyl dicarbonate, diisobutyl dicarbonate, di-tert-butyl dicarbonate and di-tert-amyl dicarbonate. With regard to the amount of the dicarbonate to be used, the stoichiometric amount with respect to the mesylated product, i.e., the equimolar amount to the mesylated product will generally be enough. The amount of the dicarbonate to be used is preferably 1 to 1.5 times as much as the stoichiometric amount with respect to the mesylated product.

The type of the catalyst is not particularly restricted as long as it is a catalyst containing palladium. Examples of the catalyst include palladium-carbon, palladium-alumina, palladium-silica and palladium-barium sulfate. Among these examples, palladium-carbon is preferable. With regard to the amount of the catalyst to be used (as the amount converted to an amount of palladium), only a small amount of the catalyst, with respect to the mesylated product, will be enough. The amount of the catalyst to be used is preferably in the range of 0.05 to 1 mass % of the mesylated product. The hydrogen pressure is not particularly restricted. The hydrogen pressure is preferably in the range of normal pressure to 1 MPa.

The reaction of the alkoxycarbonylation step (Step 5a) can be generally carried out by using a solvent. When a solvent is used, the type of the solvent is not particularly restricted unless the solvent disturbs the reaction. Examples of the solvent include: alcohols such as methanol, ethanol, 2-propanol, n-butanol and tert-butanol; esters such as ethyl acetate and ethyl propionate; ethers such as diethyl ether, tetrahydrofuran and dioxane; and hydrocarbons such as benzene, toluene and xylene. The aforementioned examples of the solvent may be used either singly or in the form of a combination of two or more types of them.

The reaction temperature may vary depending on the raw materials for the reaction (i.e., the materials involved in the reaction including the solvent). The reaction temperature is generally in the range of 30 to 80° C. The reaction time varies according to the raw materials, the reaction temperature or the like. The reaction is normally completed within 1 to 8 hours.

[Second Method]

The second method of producing an N-alkoxycarbonylpiperidine derivative comprises: a alkoxycarbonylation step (Step 4b) of reacting an N-aralkylpiperidine derivative represented by the aforementioned general formula (1) with a dicarbonate represented by the aforementioned general formula (3) in the presence of hydrogen and a catalyst containing palladium, thereby obtaining an alkoxycarbonylated product represented by the aforementioned general formula (5); and then a mesylation step (Step 5b) of reacting the alkoxycarbonylated product with a mesyl halide in the presence of a base, thereby obtaining an N-alkoxycarbonylpiperidine derivative represented by the aforementioned general formula (4).

In the alkoxycarbonylation step (Step 4b) of the second method, an N-aralkylpiperidine derivative represented by the aforementioned general formula (1) is reacted with a dicarbonate represented by the aforementioned general formula (3) in the presence of hydrogen and a catalyst containing palladium, whereby an alkoxycarbonylated product represented by the aforementioned general formula (5) is obtained. In this Step 4b, de-aralkylation and alkoxycarbonylation can be carried out in "one pot".

Examples of the dicarbonate include dimethyl dicarbonate, diethyl dicarbonate, dipropyl dicarbonate, diisopropyl dicarbonate, dibutyl dicarbonate, diisobutyl dicarbonate, di-tert-butyl dicarbonate and di-tert-amyl dicarbonate. With regard to the amount of the dicarbonate to be used, the stoichiometric amount with respect to the N-aralkylpiperidine derivative, i.e., the equimolar amount to the N-aralkylpiperidine derivative will generally be enough. The amount of the dicarbonate to be used is preferably 1 to 1.5 times as much as the stoichiometric amount with respect to the N-aralkylpiperidine derivative.

The type of the catalyst is not particularly restricted as long as it is a catalyst containing palladium. Examples of the catalyst include palladium-carbon, palladium-alumina, palladium-silica and palladium-barium sulfate. Among these examples, palladium-carbon is preferable. With regard to the amount of the catalyst to be used (as the amount converted to an amount of palladium), only a small amount of the catalyst, with respect to the N-aralkylpiperidine derivative, will be enough. The amount of the catalyst to be used is preferably in the range of 0.05 to 1 mass % of the N-aralkylpiperidine derivative. The hydrogen pressure is not particularly restricted. The hydrogen pressure is preferably in the range of normal pressure to 1 MPa.

The reaction of the alkoxycarbonylation step (Step 4b) can be generally carried out by using a solvent. When a solvent is used, the type of the solvent is not particularly restricted unless the solvent disturbs the reaction. Examples of the solvent include: alcohols such as methanol, ethanol, 2-propanol, n-butanol and tert-butanol; esters such as ethyl acetate and ethyl propionate; ethers such as diethyl ether, tetrahydrofuran and dioxane; and hydrocarbons such as benzene, toluene and xylene. The aforementioned examples of the solvent may be used either singly or in the form of a combination of two or more types of them.

The reaction temperature may vary depending on the raw materials for the reaction (i.e., the materials involved in the reaction including the solvent). The reaction temperature is generally in the range of 30 to 80° C. The reaction time varies according to the raw materials, the reaction temperature or the like. The reaction is normally completed within 1 to 8 hours.

Next, in the mesylation step (Step 5b) of the second method, the alkoxycarbonylated product obtained in the former Step 4b is reacted with a mesyl halide in the presence of a base, whereby an N-alkoxycarbonylpiperidine derivative represented by the aforementioned general formula (4) is obtained.

Examples of the mesyl halide include mesyl chloride. Examples of the base include pyridine, dimethylamine, diethylamine, triethylamine, tributylamine and triethanolamine.

With regard to the amount of the base to be used, the stoichiometric amount with respect to the mesyl halide, i.e., the equimolar amount to the mesyl halide will generally be enough. The amount of the base to be used is preferably 1 to 1.5 times as much as the stoichiometric amount with respect to the mesyl halide.

With regard to the amount of mesyl halide to be used, the stoichiometric amount with respect to the alkoxycarbonylated product, i.e., the equimolar amount to the alkoxycarbonylated product will generally be enough. The amount of mesyl halide to be used is preferably 1 to 1.5 times as much as the stoichiometric amount with respect to the alkoxycarbonylated product.

The reaction of the mesylation step (Step 5b) can be generally carried out by using a solvent. When a solvent is used, the type of the solvent is not particularly restricted unless the solvent disturbs the reaction. Examples of the solvent include: esters such as ethyl acetate and ethyl propionate; ethers such as diethyl ether, tetrahydrofuran and dioxane; hydrocarbons such as benzene, toluene and xylene; halogenated hydrocarbons such as dichloromethane, dichloroethane and chloroform; and nitrites such as acetonitrile. The aforementioned examples of the solvent may be used either singly or in the form of a combination of two or more types of them.

The reaction temperature may vary depending on the raw materials for the reaction (i.e., the materials involved in the reaction including the solvent). The reaction temperature is generally in the range of −10 to 20° C. The reaction time varies according to the raw materials, the reaction temperature or the like. The reaction is normally completed within 1 to 5 hours.

In addition, a novel compound that is useful as an intermediate of a drug, 1-(4-piperidylacetyl)-4-hydroxypiperidine represented by the following formula (10):

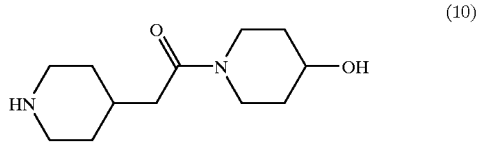

(10)

can be produced by de-aralkylation of an N-aralkylpiperidine derivative represented by the aforementioned general formula (1). The de-aralkylation reaction can be effected in the presence of hydrogen and a catalyst containing palladium.

The type of the catalyst is not particularly restricted as long as it is a catalyst containing palladium. Examples of the catalyst include palladium-carbon, palladium-alumina, palladium-silica and palladium-barium sulfate. Among these examples, palladium-carbon is preferable. With regard to the amount of the catalyst to be used (as the amount converted to an amount of palladium), only a small amount of the catalyst, with respect to the N-aralkylpiperidine derivative, will be enough. The amount of the catalyst to be used is preferably in the range of 0.05 to 1 mass % of the N-aralkylpiperidine derivative. The hydrogen pressure is not particularly restricted. The hydrogen pressure is preferably in the range of normal pressure to 1 MPa.

The reaction of the de-aralkylation can be generally carried out by using a solvent. When a solvent is used, the type of the solvent is not particularly restricted unless the solvent disturbs the reaction. Examples of the solvent include: alcohols such as methanol, ethanol, 2-propanol, n-butanol and tert-butanol; esters such as ethyl acetate and ethyl propionate; ethers such as diethyl ether, tetrahydrofuran and dioxane; and hydrocarbons such as benzene, toluene and xylene. The aforementioned examples of the solvent may be used either singly or in the form of a combination of two or more types of them.

To the contrary, an N-aralkylpiperidine derivative of the aforementioned general formula (1) may be produced by aralkylation of 1-(4-piperidylacetyl)-4-hydroxypiperidine of the formula (10).

In each of the reactions of the present invention, the target product can be separated and purified according to the conventional method after the reaction is completed. For example, purification of the target product can be effected by: extracting the target product by separation of the reaction solution; distillating the solvent off; and then purifying the target product by distillation, recrystallization, column chromatography or the like.

EXAMPLES

Hereinafter, the present invention will be further described by the following examples. It should be noted that the present invention is not restricted to these examples. The scheme of the reactions which proceeded in the examples is summarized below.

Example 1

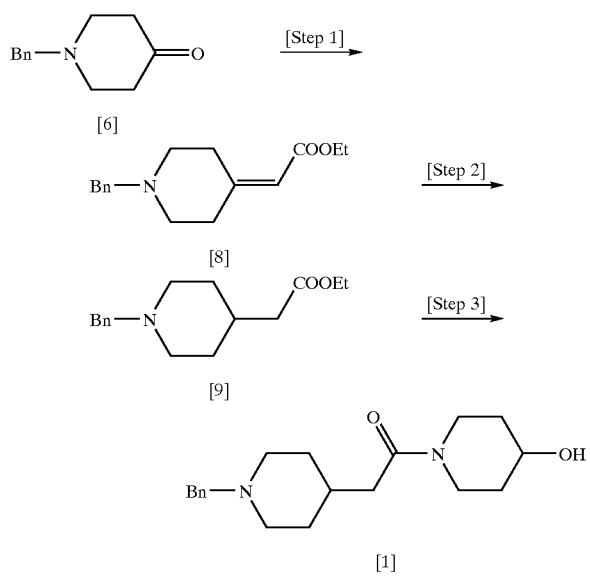

Example 2

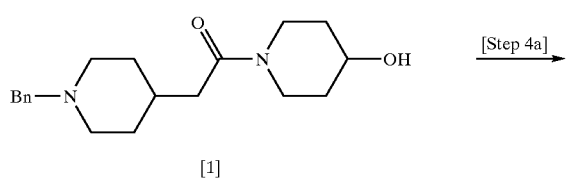

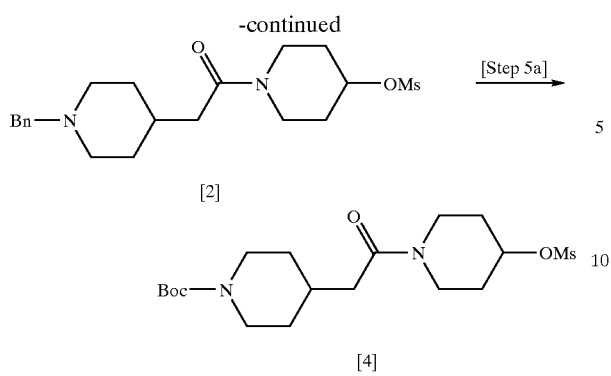

Example 3

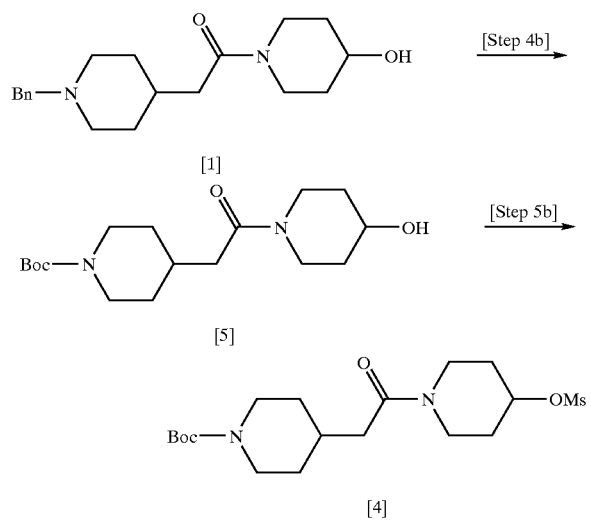

Example 4

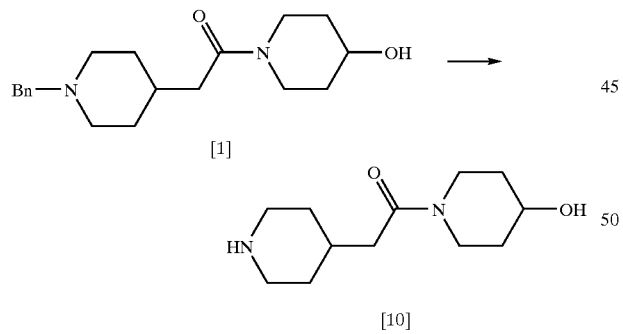

Bn = benzyl group
Boc = tert-butoxycarbonyl group
Et = ethyl group
Ms = mesyl group In each of the examples, ¹HNMR (proton nuclear magnetic resonance spectrum) and ¹³CNMR (carbon-13 nuclear magnetic resonance spectrum) are measured in $CDCl_3$ and the chemical shift δ is expressed as a shift (ppm) from tetramethylsilane to the side of the low magnetic field, In each of the examples, "s" represents a singlet, "d" represents a doublet, "t" represents a triplet, "q" represents a quadruplet, "m" represents a multiplet, and "br" represents a broad width. The coupling constant (J) is expressed by Hz. In the mass spectroscopy analysis, "EI" represents the electron impact.

Example 1

Synthesis of 1-(1-benzyl-4-piperidylacetyl)-4-hydroxypiperidine [1]

[Step 1] Synthesis of Ethyl 1-benzyl-4-piperidylideneacetate ester [8]

To a mixture of 235.4 g (1.05 mol) of Ethyl diethylphosphonoacetate, 618 g of toluene and 374.3 g of a solution of 20% sodium ethoxide in ethanol (1.10 mol as the amount of sodium ethoxide), a mixed solution of 189.3 g (1.00 mol) of 1-benzyl-4-piperidone [6] and 190 g of toluene was added dropwise at a temperature in the range of 5 to 15° C. The reaction was allowed to proceed for one hour at the temperature in the range. Thereafter, the reaction mixture was washed three times with water at room temperature. The organic layer was dried with anhydrous magnesium sulfate and then concentrated under a reduced pressure. 247.2 g of the title compound in the state of orange-color oil was obtained as the residue (the yield was 95.3%).

$^1HNMR(CDCl_3)$δ(ppm): 1.26(t, J=7.1 Hz,3H), 2.31(m, 2H), 2.51(m,4H), 2.99(m,2H), 3.51(s,2H), 4.13(q,J=7.1 Hz,2H), 5.63(s,1H), 7.31(m,5H).

$^{13}CNMR(CDCl_3)$δ(ppm): 14.54, 29.67, 37.04, 54.33, 54.76, 59.78, 62.82, 114.26, 127.30, 128.47, 129.27, 138.57, 159.80, 166.77.

[Step 2] Synthesis of ethyl 1-benzyl-4-piperidylacetate ester [9]

7.79 g (0.030 mol) of ethyl 1-benzyl-4-piperidylideneacetate [8] ester and 43 g of 2-propanol were mixed with each other. To the obtained solution, 0.39 g of 3% platinum-carbon (containing water at 50% content) was added. The reaction was allowed to proceed for 6 hours at 55° C. under the hydrogen pressure of 0.4 to 0.5 MPa. The resultant reaction mixture was cooled to room temperature, the catalyst was removed by filtration therefrom, and the filtrate was concentrated under a reduced pressure, whereby 7.65 g of the title compound in the state of colorless oil was obtained as the residue (the yield was 97.6%).

$^1HNMR(CDCl_3)$δ(ppm): 1.23(t,J=7.1 Hz,3H), 1.31(m, 2H), 1.67(m,2H), 1.78(m,1H), 1.97(m,2H), 2.21(d,J=7.2 Hz,2H), 2.85(m,2H), 3.47(s,2H), 4.11(q,J=7.1 Hz,3H), 7.29 (m,5H) $^{13}CNMR(CDCl_3)$δ(ppm)): 14.51, 32.34, 33.19, 41.50, 53.75, 60.36, 63.62, 127.11, 128.36, 129.37, 138.79, 172.98.

[Step 3] Synthesis of 1-(1-benzyl-4-piperidylacetyl)-4-hydroxypiperidine [1]

7.84 g (0.030 mol) of ethyl 1-benzyl-4-piperidylacetate ester [9], 4.25 g (0.042 mol) of 4-hydroxypiperidine, 6.96 g of a solution of 28% sodium methoxide in methanol (0.036 mol as the amount of sodium methoxide) and 26 g of toluene were mixed with each other, and the temperature of the mixture was increased. The reaction was allowed to proceed for 5.5 hours at a reflux temperature of 90° C. After the reaction was completed, the reaction mixture was cooled to room temperature and an aqueous solution of sodium chloride was added thereto. Further, 13.1 g of 10% hydrochloric acid was added to the mixture. Extraction was carried out by using ethyl acetate, and the resultant organic layer was dried with anhydrous magnesium sulfate and concentrated under a reduced pressure. 9.26 g of the concentrated residue was obtained.

To 68.9 g of the concentrated residue obtained in a process similar to that described above, 180 g of ethyl acetate was added. The concentrated residue was dissolved in ethyl acetate by heating, and then the mixture was cooled to room temperature and subjected to filtration. The resultant wet crystal was dried under a reduced pressure, whereby 50.7 g of the title compound in the state of white powder was obtained (the yield was 73.6%).

$^1$HNMR(CDCl$_3$)δ(ppm): 1.30(m,2H), 1.47(m,2H), 1.71 (m,2H), 1.82(m,3H), 2.25(d,J=7.0 Hz,2H), 2.25(br,1H), 2.86 (m,2H), 3.18(m,2H), 3.48(s,2H), 3.73(m,1H), 3.90(m,1H), 4.09(m,1H), 7.30(m,5H).

$^{13}$CNMR(CDCl$_3$)δ(ppm): 32.58, 33.42, 34.25, 34.90, 39.19, 39.88, 43.36, 53.86, 63.64, 67.25, 127.17, 128.37, 129.50, 138.56, 170.73.

Mass spectrometry (EI): 316 (M).

Example 2

Synthesis of 1-(1-tert-butoxycarbonyl-4-piperidylacetyl)-4-mesyloxypiperidine [4]

[Step 4a] Synthesis of 1-(1-benzyl-4-piperidylacetyl)-4-mesyloxypiperidine [2]

To a mixture of 4.75 g (0.015 mol) of 1-(1-benzyl-4-piperidylacetyl)-4-hydroxypiperidine [1], 51 g of toluene, 1.68 g (0.017 mol) of triethylamine, 1.87 g (0.016 mol) of mesyl chloride was added dropwise at a temperature in the range of 0 to 10° C. and the reaction was allowed to proceed for 2 hours at the temperature in the range. Thereafter, the reaction mixture was washed with an aqueous solution of sodium hydrogencarbonate and an aqueous solution of sodium chloride. The resultant organic layer was dried with anhydrous magnesium sulfate and concentrated under a reduced pressure. To the concentrated residue, 7 g of 2-propanol and 43 g of diisopropyl ether were added and the temperature of the mixture was increased. The mixture was stirred for 0.3 hours at a reflux temperature of 66° C. Thereafter the mixture was cooled to room temperature and subjected to filtration. The resultant wet crystal was dried under a reduced pressure, whereby 5.01 g of the title compound in the state of white powder was obtained (the yield was 84.7%).

$^1$HNMR(CDCl$_3$)δ(ppm): 1.30(m,2H), 1.71(m,2H), 1.83 (m,3H), 1.99(m,4H), 2.25(d,J=7.0 Hz,2H), 2.86(m,2H), 3.05 (s,3H), 3.40(m,1H), 3.48(s,2H), 3.54(m,1H), 3.68(m,1H), 3.85(m,1H), 4.94(m,1H), 7.30(m,5H).

$^{13}$CNMR(CDCl$_3$)δ(ppm): 31.67, 32.68, 33.38, 38.37, 39.07, 39.81, 42.54, 53.86, 63.64, 77.13, 127.13, 128.37, 129.40, 138.79, 170.72.

Mass spectrometry (EI): 394 (M).

Differential scanning calorimetry: 100.3° C.

[Step 5a] Synthesis of 1-(1-tert-butoxycarbonyl-4-piperidylacetyl)-4-mesyloxypiperidine [4]

3.95 g (0.01 mol) of 1-(1-benzyl-4-piperidylacetyl)-4-mesyloxypiperidine [2], 2.18 g (0.01 mol) of di-tert-butyl dicarbonate and 33.4 g of 2-propanol were mixed with each other, and the temperature of the mixture was increased to 50° C. To this mixture, 0.79 g of 5% palladium-carbon (containing water at 50% content) was added. The reaction was allowed to proceed for 2 hours at 50° C. under hydrogen pressure of 0.5 MPa. The resultant reaction mixture was cooled to room temperature, the catalyst was removed by filtration therefrom, and the filtrate was concentrated under a reduced pressure. 27 g of toluene was added to the concentrated residue, the temperature of the mixture was increased to 50° C., and then the mixture was washed with an aqueous solution of sodium chloride. The resultant organic layer was concentrated under a reduced pressure. 14.1 g of toluene was added to the concentrated residue. The crystals which precipitated at room temperature were collected by filtration and dried under a reduced pressure, whereby 3.23 g of the title compound in the state of white crystalline powder was obtained as the residue (the yield was 79.8%).

$^1$HNMR(CDCl$_3$)δ(ppm): 1.13(m,2H), 1.45(s,9H), 1.72 (m,2H), 1.9(m,5H), 2.25(d,J=7.2 Hz,2H), 2.73(m,2H), 3.06 (s,3H), 3.41(m,1H), 3.56(m,1H), 3.69(m,1H), 3.85(m,1H), 4.08(m,2H), 4.95(m,1H).

$^{13}$CNMR(CDCl$_3$)δ(ppm): 28.67, 31.62, 32.42, 32.63, 33.40, 38.39, 39.05, 39.65, 42.42, 43.88, 77.02, 79.54, 155.04, 170.23.

Mass spectrometry (EI): 404 (M).

Example 3

Synthesis of 1-(1-tert-butoxycarbonyl-4-piperidylacetyl)-4-mesyloxypiperidine [4]

[Step 4b] Synthesis of 1-(1-tert-butoxycarbonyl-4-piperidylacetyl)-4-hydroxypiperidine [5]

158.2 g (0.50 mol) of 1-(1-benzyl-4-piperidylacetyl)-4-hydroxypiperidine [1], 109.1 g (0.50 mol) of di-tert-butyl dicarbonate and 1315 g of 2-propanol were mixed with each other. To this mixture, 31.6 g of 5% palladium-carbon (containing water at 50% content) was added. The reaction was allowed to proceed for 7.5 hours at a temperature in the range of room temperature to 50° C. under the flow of hydrogen. The catalyst was removed by filtration therefrom, and the filtrate was concentrated under a reduced pressure. 830 g of toluene was added to the concentrated residue, and then the mixture was washed with an aqueous solution of sodium chloride. The resultant organic layer was concentrated under a reduced pressure. 337 g of toluene was added to the concentrated residue and the temperature of the mixture was increased. After the residue was dissolved in toluene, the mixture was cooled to room temperature. The crystals which precipitated at room temperature were collected by filtration and the resultant wet crystals were dried under a reduced pressure, whereby 130.1 g of the title compound in the state of white powder was obtained (the yield was 88.6%).

$^1$HNMR(CDCl$_3$)δ(ppm): 1.13(m,2H), 1.45(s,9H), 1.49 (m,2H), 1.71(m,2H), 1.87(m,2H), 1.99(m,1H), 2.25(m,2H), 2.26(s,1H), 2.72(m,2H), 3.21(m,2H), 3.74(m,1H), 3.93(m, 1H), 4.08(m,4H).

$^{13}$CNMR(CDCl$_3$)δ(ppm): 28.67, 32.43, 33.50, 34.19, 34.86, 39.18, 39.74, 43.23, 44.05, 67.21, 79.57, 155.08, 170.21.

Mass spectrometry (EI): 326 (M).

[Step 5b] Synthesis of 1-(1-tert-butoxycarbonyl-4-piperidylacetyl)-4-mesyloxypiperidine [4]

To 16.3 g (0.05 mol) of 1-(1-tert-butoxycarbonyl-4-piperidylacetyl)-4-hydroxypiperidine [5], 147.1 g of toluene and 6.58 g (0.065 mol) of triethylamine were added. 6.30 g (0.055 mol) of mesyl chloride was added dropwise to the mixture at a temperature in the range of 0 to 5° C. and the reaction was allowed to proceed for 2 hours at the temperature in the range. Toluene was added to the reaction mixture. Thereafter, the reaction mixture was washed with an aqueous solution of sodium hydrogencarbonate and an aqueous solution of sodium chloride, and concentrated under a reduced pressure. 70.8 g of toluene was added to the concentrated residue, and the temperature of the mixture was increased. After the residue was dissolved in toluene, filtration was carried out. Thereafter, the filtrate was cooled to room temperature and the crystals which precipitated at room temperature were collected by filtration. The resultant wet crystals were dried under a reduced pressure, whereby 17.2 g of the title compound in the state of white crystalline powder was obtained (the yield was 84.8%). The values obtained by the analysis of $^1$HNMR, $^{13}$CNMR and mass spectroscopy were substantially the same as those obtained in Step 5a of Example 2.

Example 4

Synthesis of 1-(4-piperidylacetyl)-4-hydroxypiperidine [10]

14.2 g (0.05 mol) of 1-(1-benzyl-4-piperidylacetyl)-4-hydroxypiperidine [1] and 127.9 g of 2-propanol were mixed with each other. To this mixture, 1.42 g of 5% palladium-carbon (containing water at 50% content) was added. The reaction was allowed to proceed for 14 hours at 50° C. under the flow of hydrogen. The catalyst was removed by filtration therefrom, and the filtrate was concentrated under a reduced pressure. 23.6 g of acetonitrile was added to the concentrated residue, and the temperature of the mixture was increased to a reflux temperature of 80° C. The crystals which precipitated at room temperature were collected by filtration and the resultant wet crystals were dried under a reduced pressure, whereby 9.08 g of the title compound in the state of white powder was obtained (the yield was 89.4%).

$^1$HNMR(CDCl$_3$)δ(ppm): 1.18(m,2H), 1.48(m,2H), 1.74(m,2H), 1.87(m,2H), 1.94(m,1H), 2.25(d,J=6.40 Hz,2H), 2.63(m,2H), 2.74(br,2H), 3.05(m,2H), 3.18(m,2H), 3.74(m,1H), 3.89(m,1H), 4.11(m,1H).

$^{13}$CNMR(CDCl$_3$)δ(ppm): 33.54, 33.73, 34.32, 35.01, 39.26, 40.41, 43.40, 46.60, 66.96, 170.43.

Mass spectrometry (EI): 226 (M).

Differential scanning calorimetry: 130.3° C.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A method of producing an N-alkoxycarbonylpiperidine derivative represented by the following general formula (4):

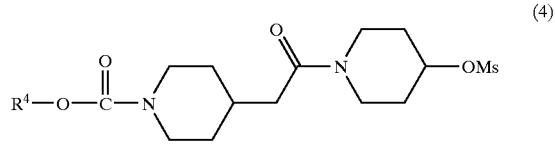

(4)

wherein R$^4$ represents an alkyl group and Ms represents a mesyl group, comprising:

reacting an N-aralkylpiperidine derivative represented by the following general formula (1):

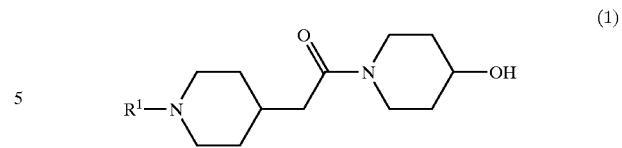

(1)

wherein R$^1$ represents an aralkyl group which may have a substituent, with a mesyl halide in the presence of a base, thereby obtaining a mesylated product represented by the following general formula (2):

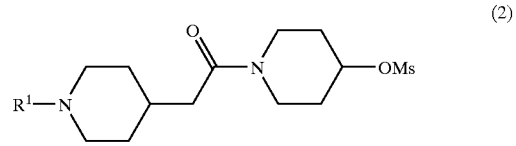

(2)

wherein R$^1$ represents an aralkyl group which may have a substituent and Ms represents a mesyl group; and reacting the mesylated product with a dicarbonate represented by the following general formula (3):

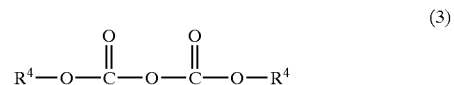

(3)

wherein R$^4$ represents an alkyl group, in the presence of hydrogen and a catalyst containing palladium, thereby obtaining an N-alkoxycarbonylpiperidine derivative represented by the following general formula (4):

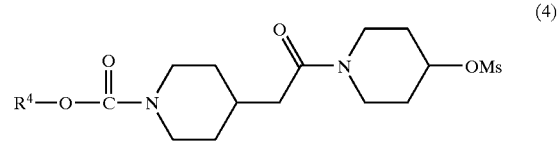

(4)

wherein R$^4$ represents an alkyl group and Ms represents a mesyl group.

2. A method of producing an N-alkoxycarbonylpiperidine derivative represented by the following general formula (4):

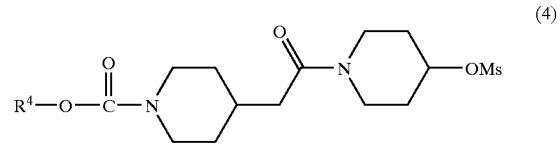

(4)

wherein R$^4$ represents an alkyl group and Ms represents a mesyl group, comprising:

reacting an N-aralkylpiperidine derivative represented by the following general formula (1):

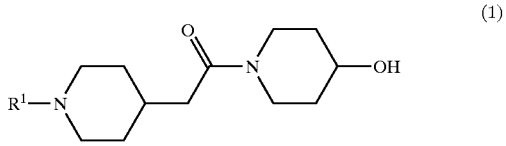

(1)

wherein R$^1$ represents an aralkyl group which may have a substituent, with a dicarbonate represented by the following general formula (3):

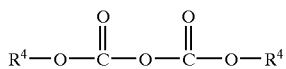

wherein $R^4$ represents an alkyl group, in the presence of hydrogen and a catalyst containing palladium, thereby obtaining an alkoxycarbonylated product represented by the following general formula (5):

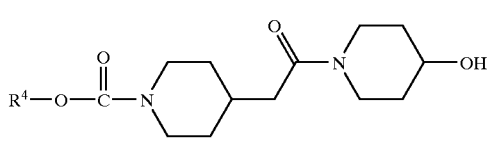

wherein $R^4$ represents an alkyl group; and
reacting the alkoxycarbonylated product with a mesyl halide in the presence of a base, thereby obtaining an N-alkoxycarbonylpiperidine derivative represented by the following general formula (4):

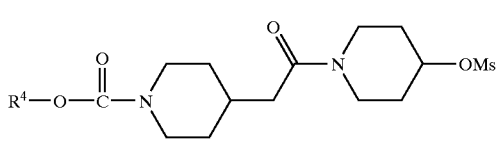

wherein $R^4$ represents an alkyl group and Ms represents a mesyl group.

3. An N-aralkylpiperidine derivative represented by the following general formula (1):

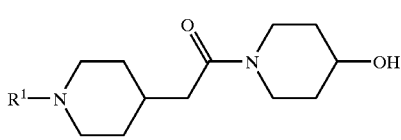

wherein $R^1$ represents an aralkyl group which may have a substituent.

4. A method of producing an N-aralkylpiperidine derivative represented by the following general formula (1):

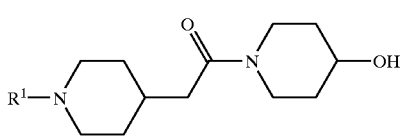

wherein $R^1$ represents an aralkyl group which may have a substituent, comprising:
reacting an N-aralkylpiperidone derivative represented by the following general formula (6):

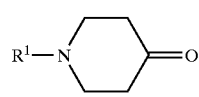

wherein $R^1$ represents an aralkyl group which may have a substituent, with a phosphate reagent represented by the following general formula (7):

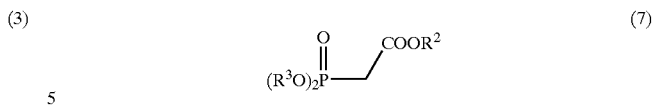

wherein $R^2$ represents an alkyl group and $R^3$ represents an alkyl group or aryl group, in the presence of a base, thereby obtaining a piperidylideneacetic acid derivative represented by the following general formula (8):

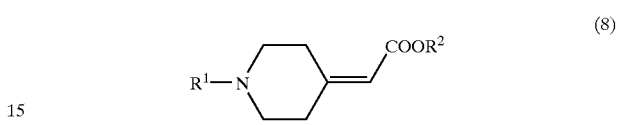

wherein $R^1$ represents an aralkyl group which may have a substituent and $R^2$ represents an alkyl group;
reducing the piperidylideneacetic acid derivative to a piperidylacetic acid derivative represented by the following general formula (9):

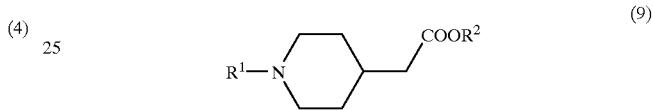

wherein $R^1$ represents an aralkyl group which may have a substituent and $R^2$ represents an alkyl group; and
reacting the piperidylacetic acid derivative with 4-hydroxypiperidine in the presence of a base, thereby obtaining an N-aralkylpiperidine derivative represented by the following general formula (1):

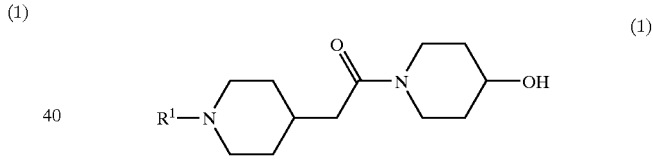

wherein $R^1$ represents an aralkyl group which may have a substituent.

5. The method according to claim 1, wherein $R^1$ represents a benzyl group which may have a substituent.

6. The method according to claim 1, wherein $R^1$ represents a benzyl group.

7. The method according to claim 1, wherein $R^4$ represents a straight-chain or branched alkyl group having 1 to 6 carbon atoms.

8. The method according to claim 1, wherein $R^4$ represents a t-butyl group.

9. The method according to claim 1, wherein $R^1$ represents a benzyl group, and $R^4$ represents a t-butyl group.

10. The method according to claim 2, wherein $R^1$ represents a benzyl group which may have a substituent.

11. The method according to claim 2, wherein $R^1$ represents a benzyl group.

12. The method according to claim 2, wherein $R^4$ represents a straight-chain or branched alkyl group having 1 to 6 carbon atoms.

13. The method according to claim 2, wherein $R^4$ represents a t-butyl group.

14. The method according to claim 2, wherein $R^1$ represents a benzyl group, and $R^4$ represents a t-butyl group.

15. The N-aralkylpiperidine derivative according to claim 3, wherein $R^1$ represents a benzyl group which may have a substituent.

16. The N-aralkylpiperidine derivative according to claim 3, wherein $R^1$ represents a benzyl group.

17. The method according to claim 4, wherein $R^1$ represents a benzyl group which may have a substituent.

18. The method according to claim 4, wherein $R^1$ represents a benzyl group.

19. The method according to claim 4, wherein $R^2$ represents a methyl group or ethyl group, and $R^3$ represents a methyl group, ethyl group or phenyl group.

20. The method according to claim 4, wherein $R^1$ represents a benzyl group, $R^2$ represents a ethyl group, and $R^3$ represents a ethyl group.

21. A method of producing 1-(4-piperidylacetyl)-4-hydroxypiperidine represented by the following formula (10):

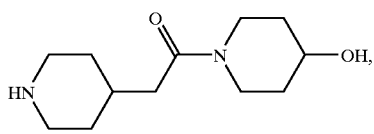

(10)

comprising:

de-aralkylating an N-aralkylpiperidine derivative of the following general formula (1):

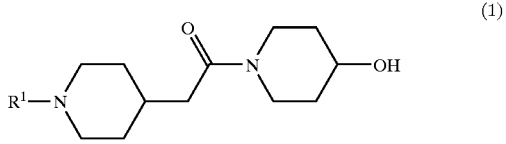

(1)

wherein $R^1$ represents an aralkyl group which may have a substituent.

22. 1-(4-piperidylacetyl)-4-hydroxypiperidine represented by the following formula (10):

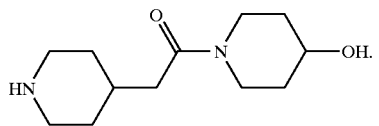

(10)

* * * * *